United States Patent [19]

Tsubakino

[11] Patent Number: 5,601,718
[45] Date of Patent: Feb. 11, 1997

[54] METHOD OF MAKING A FILTER FOR PREPARATIONS

[75] Inventor: Motohiro Tsubakino, Himeji, Japan

[73] Assignee: Taiho Industries Co., Ltd., Tokyo, Japan

[21] Appl. No.: 449,374

[22] Filed: May 24, 1995

Related U.S. Application Data

[62] Division of Ser. No. 201,190, Feb. 24, 1994, Pat. No. 5,547,571.

[30] Foreign Application Priority Data

Feb. 26, 1993 [JP] Japan ................................ 5-061279

[51] Int. Cl.⁶ .......................... B01D 35/00; G01N 33/48
[52] U.S. Cl. .......................... 210/495; 156/250; 210/232; 210/506; 264/DIG. 48; 422/58
[58] Field of Search ................................ 210/232, 542, 210/495, 496, 483, 506; 156/163, 211, 250, 380.2; 264/DIG. 48; 422/55, 56, 57, 61, 101, 104; 435/30, 805

[56] References Cited

U.S. PATENT DOCUMENTS

| | | | |
|---|---|---|---|
| 2,282,301 | 5/1942 | Petersen | 210/495 |
| 3,990,850 | 11/1976 | Friedman et al. | 422/55 |
| 4,789,629 | 12/1988 | Baker et al. | 422/56 |
| 4,818,677 | 4/1989 | Hay-Kaufman et al. | 422/56 |
| 5,064,766 | 11/1991 | Wardlaw et al. | 422/56 |
| 5,104,619 | 4/1992 | de Castro et al. | 422/101 |
| 5,106,582 | 4/1992 | Baker | 422/56 |

*Primary Examiner*—John Kim
*Attorney, Agent, or Firm*—Varndell Legal Group

[57] ABSTRACT

The invention is directed to a method for making filter preparations including a filter sheet for receiving specimens thereon. The method includes cutting a flexible sheet of material to form a filter frame, and slitting the filter frame to form two slits with a central hole therebetween. The two slits define inner edges of parallel framing parts in the filter frames and outer edges of a presser part. One end of the presser part is pulled upward, and the filter sheet is inserted between the presser parts and the parallel framing parts. Then, the presser part is released downward and restored to its original position, so that the filter sheet contacts an undersurface of the presser part and is contained in the slits between the presser part and the parallel framing parts. The filter sheet also adheres to an upper surface of the parallel framing parts and a portion of the filter sheet is exposed through the central hole for receiving mounting specimens thereon.

1 Claim, 4 Drawing Sheets

METHOD OF MAKING A FILTER FOR PREPARATIONS

CROSS-REFERENCE TO RELATED APPLICATION

This application is a divisional application of U.S. Ser. No. 08/201,190, filed Feb. 24, 1994, now U.S. Pat. No. 5,547,571.

BACKGROUND OF THE INVENTION

1. Field of the Invention

The present invention relates to a filter for preparations used to mount specimens such as cells on a glass slide, and a method of making and using same.

2. Prior Art

In medical diagnosis, conventionally cells or their reaggregate are sampled from human bodies for the purpose of performing, for example, cytological diagnosis of cancer, subjected to a staining treatment and then mounted on a glass slide with a sealing medium and a glass cover to make a preparation for microscopic observation. In such an observation, a filter is widely used to separate specimens for making preparations.

Typically, conventional preparations are made as shown in FIGS. 6(a) to 6(c). According to the conventional procedure shown in FIGS. 6(a) to 6(c), specimens (WP) are mounted on a filter (FT) which has been applied to the under surface of a frame (FR) of a filter assembly (F) by means of an adhesive having less bearable property to solvents such as xylene, with foreign materials separated or removed therefrom using a suction or pressurizing means to only leave the specimens on the filter (FT). The specimen are fixed thereon by means of an alcohol to prevent their release from the filter (FT). The specimens (WP) are then stained with desirable color for a specific observation in a stain bath (not shown), impregnated with an organic solvent such as xylene to fix them completely on the filter and set on a glass slide (SG) as shown in FIG. 6(a). As described above, an adhesive having less bearable property to solvents is used to bond the frame (FR) and the filter (FT) to facilitate their separation in the subsequent step, where xylene, for example, actually loosens their bond. Under such a condition, it is easy to remove the frame (FR) and leave the specimens and the filter (FT) on the glass slide (SG) when an extended part (FT) of the filter (FT) is picked up with a pair of pincettes (PS) in the arrow direction shown III in FIG. 6(b). An adequate amount of sealing medium (SM) is then added dropwise over the specimens (WP) which is covered with a cover glass (CG), as shown in FIG. 6(c), to complete a preparation (P).

As only the specimens (WP) are secured on the filter (FT), it is possible to carry out microscopic observations accurately and safely without any specific skill even when conventional preparations are used. However there exists, problems inherent in such preparations which should be solved.

The first disadvantage is that the adhesive having less bearable property to solvents such as xylene is often dissolved unexpectedly in the stain to cause a premature separation of the frame (FR) and the filter (FT) during the staining treatment step and that it is still necessary to use xylene, for example, to loosen their bond.

Secondarily, the specimens (WP) along with the filter (FT) are often irregularly strained when the extended part (ft) of the filter (FT) is picked up to separate the frame (FR) and the filter (FT), which tends to result in imprecise observations.

Further, as the frame (FR) and the filter (FT) are adhered to each other over relatively wider area, the behavior of the sealing medium on the filter (FT) is not uniform, i.e., its behavior around the specimens (WP) is quite different from that in the other areas of the filter (FT). This might result in a serious inconvenience upon microscopic observations because of a deflection caused by such ununiformity of the sealing medium on the filter (FT).

It has been required by those who are engaged in cytological diagnosis to develop a filter which enables easier making of preparations without contamination of their fingers due to the sealing medium seepage or the like.

SUMMARY OF THE INVENTION

Accordingly, it is an object of the present invention to provide an easier and safer filter for making preparations. The most characteristic feature of the present invention will be described in the following.

According to the present invention, the above mentioned and further objects can be accomplished by providing:

(1) A filter for preparations including of a sheet form filter frame made of flexible material such as synthetic resins and a porous filter sheet, in which the filter frame has an external size suitable to set on a glass slide and is slit to form an open-sided presser part with an opening bored therethrough and parallel framing parts. The filter sheet is applied to the under surface of the presser part, passed through both slits between the presser part and the parallel framing parts, both tips of said filter sheet are adhered on the upper surface of the parallel framing parts, thereby the filter sheet being exposed through the opening for mounting specimens thereon;

(2) A method of making a filter for preparations which comprises cutting out a filter frame of an external size suitable to set on a glass slide from a flexible sheet form material such as synthetic resins by means of a press or the like and slitting the filter frame to form at least an open-sided presser part with an opening bored therethrough and parallel framing parts, pulling up the presser part to insert a porous filter sheet between the presser part and the parallel framing parts and then releasing downward and restoring the presser part to attach the filter sheet to the under surface of the presser part, passed through both slits between the presser part and the parallel framing parts, both tips of said filter sheet being adhered on the upper surface of the parallel framing parts, thereby the filter sheet is exposed through the opening for mounting specimens thereon; and (3) A method of using a filter for preparations with a filter sheet which comprises mounting specimens on a filter sheet attached to a filter frame made of flexible material such as synthetic resins, setting the filter frame on a glass slide after staining and fixing treatments thereof, pulling up the filter frame while pressing a presser part provided with an opening bored there through so as to shear off the filter sheet between the presser part and the parallel framing parts, and then releasing the presser part to remove the filter frame from the glass slide and only leave the remainder of the filter sheet with the specimens mounted thereon.

As described above, when making the filter of the present invention, a filter sheet is inserted between a presser part and parallel framing parts after the presser part is released downward and restored, both tips of the filter sheet are then adhered on the upper surface of the parallel framing parts to form an integral filter, thereby the filter sheet is exposed through an opening for mounting specimens. When using the present filter, the filter frame is pulled up while pressing the presser part to shear off the filter sheet and leave the rest of the filter sheet with the specimens mounted thereon. Because of such an improved construction of the present invention, operators can easily make preparations without contamination.

DETAILED DESCRIPTION AND THE PREFERRED EMBODIMENTS

Referring to the accompanying drawings, preferred embodiments will be described in the following.

1. Filter

Figure 1:
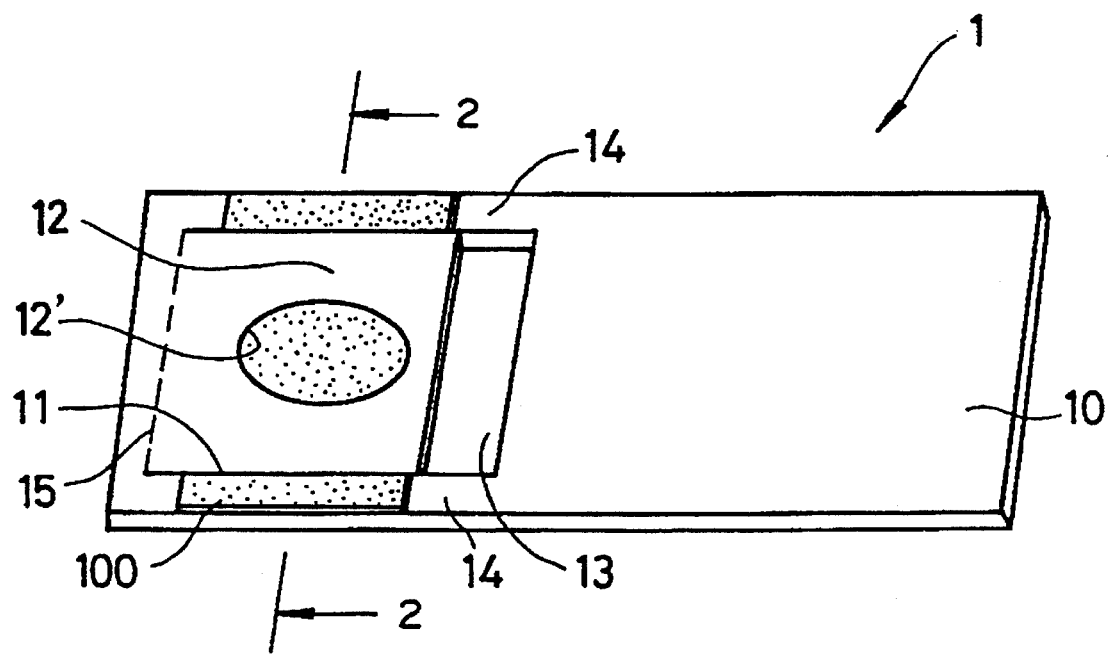
FIG. 1 is a perspective view of a filter of the present invention.

Reference is directed to a perspective view of the filter of the present invention (FIG. 1) and a section view (FIG. 2) taken on line 2—2 in FIG. 1. The filter 1 comprises a sheet form filter frame 10 having a base frame in the form of a sheet that is made of flexible material such as synthetic resins and a porous filter sheet 100. The filter frame 10 has an external size suitable to set on a glass slide. An open-sided presser part 12 and a hole or internal opening in the base frame 13 are formed by a slits 11. A central opening 12' is also provided. The filter sheet 100 is applied to the under surface of the presser part 12 and both tips 101 are inserted through the slits 11 and then adhered on the upper surface of parallel framing parts 14 by means of bonding, welding and the like. The filter sheet 100 is thus exposed through the central opening 12' of the presser part 12.

Dotted line 15 shows a concave slot useful for releasing the presser part 12 upward.

2. How to make the filter (a) Preparatory process of the filter frame 10

A high heat- and chemical-resistant as well as flexible resin sheet is useful as the material of the filter frame 10 that is later combined with the filter sheet 100. Such a resin sheet is cut out to an external size similar to that of a standard glass slide, and then the open-sided presser part 12 with the central opening 12' bored therethrough and the hole or internal opening 13 are formed all at once by the slits 11 along the lengthwise direction to complete the filter frame 10.

The surface of the filter frame 10 is then subjected to a cleaning treatment with alcohols or surfactants. Finally, an adhesive such as silicone gum is coated on the contact surface of the presser part 12 with the filter sheet 100.

(b) Preparatory process of the filter sheet 100

Polycarbonate can be used as the material of the filter sheet 100. As polycarbonate adsorbs fine dust because of its static characteristics, the surface of the material should be washed thoroughly with volatile solvents such as alcohols, xylene and the like or surfactants so as to prevent unstable observations due to the dust.

c) Assembly of the filter

Figure 2:
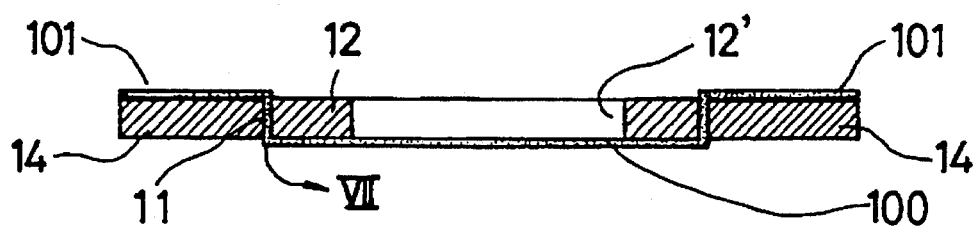
FIG. 2 is a section view taken on line 2—2 in FIG. 1.
Figure 3:
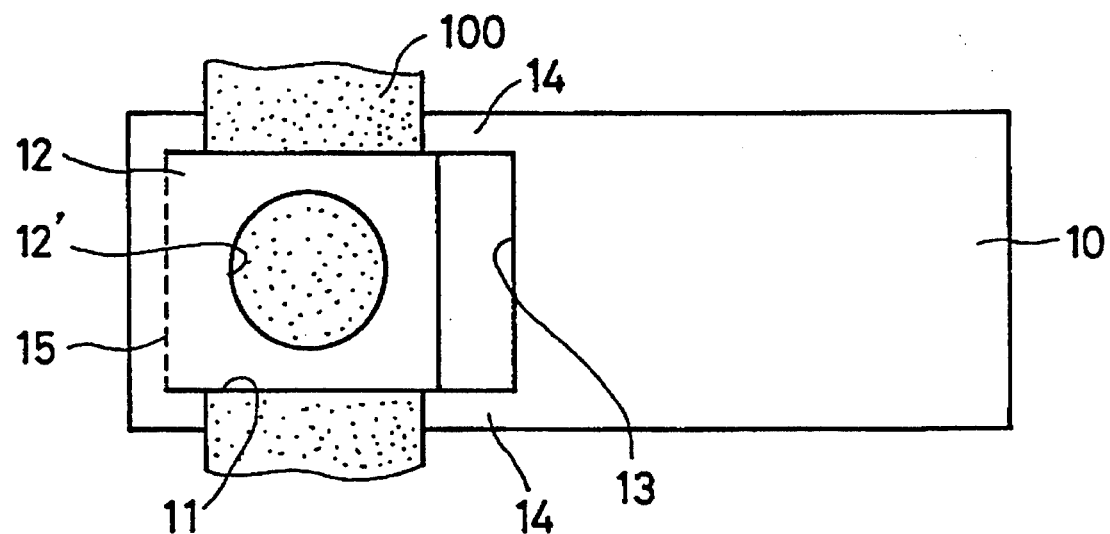
FIG. 3 is a plan view showing an assembling procedure of the filter shown in FIG. 1.
Figure 4:
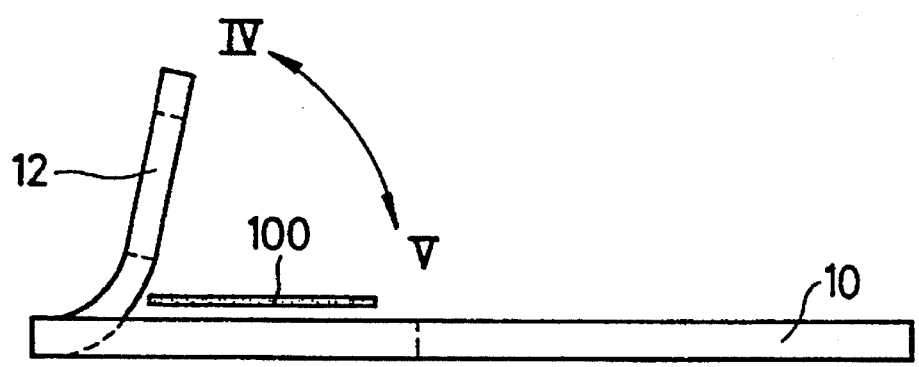
FIG. 4 is a section view of the filter shown in FIG.

Referring now to FIG. 4, the presser part 12 is released downward and restored in the arrow direction from IV to V with its restoring force after the filter sheet 100 has been passed between the presser part 12 and the filter frame 10. This results in a rigid insertion of the filter sheet 100 in the filter frame 10 as shown in FIG. 2. The filter sheet 100 is adhered to the under surface of presser part 12 by means of the adhesive which has been coated thereon, while its both tips 101 are also adhered on the upper surface of parallel framing parts 14. Finally, both sides of the filter sheet 100 extending beyond of the filter frame 10 are cut down to make its width fit the filter frame 10. The filter assembly 1 shown in FIG. 1 is thus completed.

The filter frame 10 and the filter sheet 100 may be thermally welded in a manner other than adhesion by means of adhesives. Further, the filter sheet 100 may be applied merely to the under surface of the filter frame 10 and adhered only to the under surface of the parallel framing parts 14, which results in a favorable result similarly.

3. How to use the filter assembly 1

Referring back to FIG. 1 again, how to use the filter assembly 1 is described in the following.

Figure 5A:
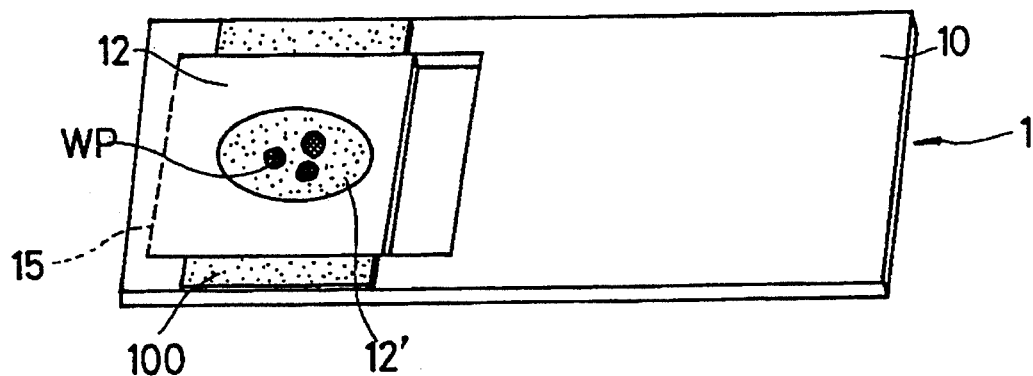
FIG. 5(a) is a perspective view showing the first step of using procedure of the filter shown in FIG. 1.

An adequete amount of specimens (WP) of cells and the like are placed on the filter sheet 100 at the area of the opening 12' of the filter assembly 1 and held thereon as shown in FIG. 5(a) with foreign materials fully separated therefrom by means of suction or the like. Then, the specimens (WP) are rigidly fixed on the filter sheet 100 with a fixative such as ethanol, followed by washing and staining treatments. The filter assembly 1 thus prepared is set on a standard glass slide (SG) of similar size. See FIG. 5(b).

Figure 5B:
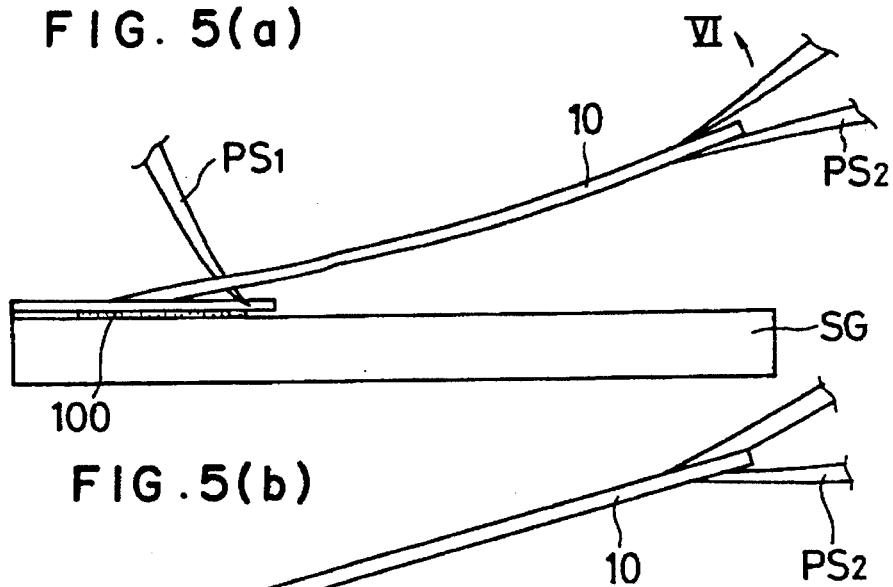
FIG. 5(b) is a section view showing the second step of FIG. 5(a).

While pressing downward or fixing the presser part 12 by means of any convenient rod or a pair of pincettes ($PS_1$), the opposite edge of the filter frame 10 is carefully picked up in the direction of arrow IV using another pair of pincettes ($PS_2$) as shown in FIG. 5(b). In this situation, the filter frame 10 is kept upward leaving only the presser part 12 on the glass slide (SG). In this manner the filter sheet 100 is adhered to the upper surface of the parallel framing parts 14 to form an integral structure and also to the under surface of the presser part 12 (cf. FIG. 2). It is then simple sheared off along a line VII between the presser part 12 and the parallel framing parts 14 to leave it under the presser part 12.

Figure 5C:
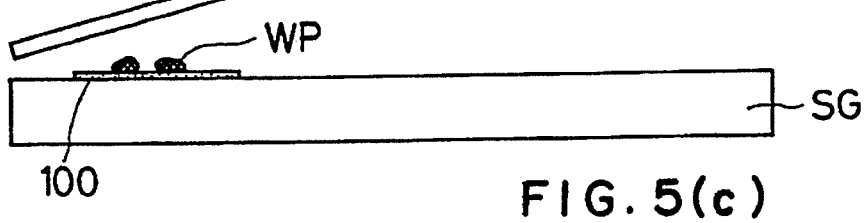
FIG. 5(c) is a section view showing the third step of FIG. 5(a).
Figure 5D:
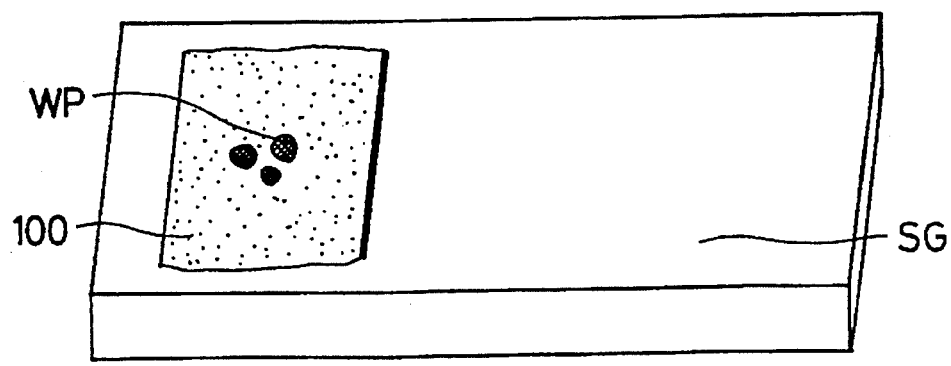
FIG. 5(d) is a perspective view showing the filter sheet with specimens after removing the filter shown in FIG. 5(a).
Figure 6A:
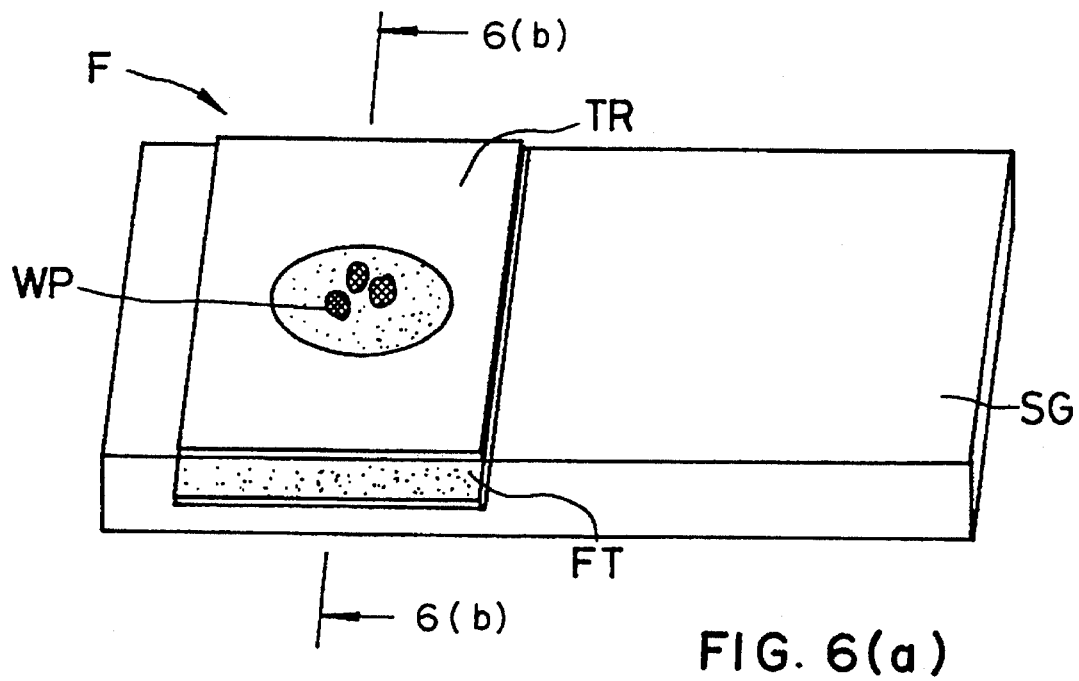
FIG. 6(a) is a perspective view showing the first step of a conventional preparation making procedure.
Figure 6B:
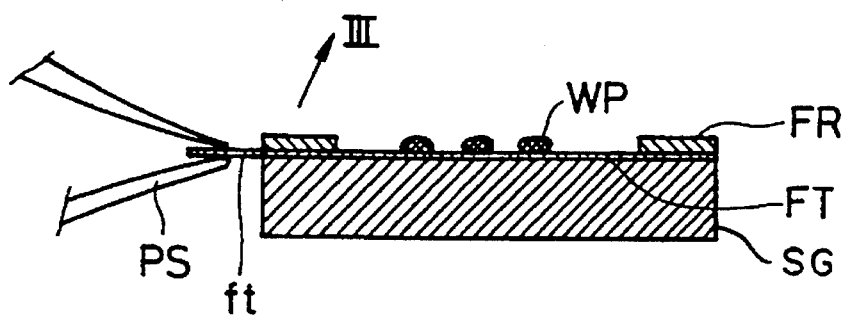
FIG. 6(b) is a section view taken on line 6(b)—6(b) in FIG. 6(a) showing the second step thereof.
Figure 6C:
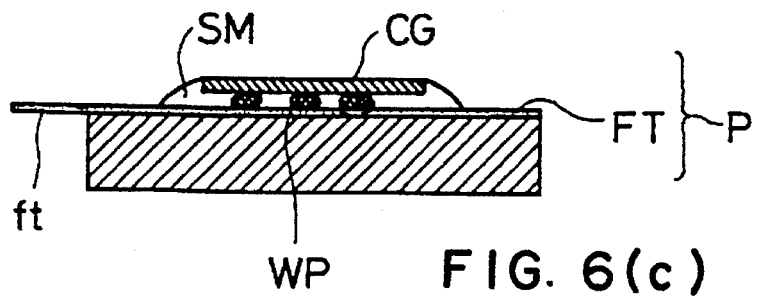
FIG. 6(c) is a section view taken on line 6(b)—6(bb) in FIG. 6(a) showing the third step thereof.

When the presser part 12 is thereafter released upward, the filter frame 10 is detached from the glass slide (SG) as a whole, as shown in FIG. 5(c), and the rest of the filter sheet 100 with the specimens (WP) fixed thereon are left on the glass slide (SG). An adequete sealing medium (SM) is then applied to the filter sheet 100 left on the glass slide (SG), and the specimen (WP) is covered with a glass cover (not shown) to give the desired preparation. A representative sealing medium (SM) can be made by dissolving (A) into (B), and adding (C) thereto, if desired, where:

(A) is a macromolecular polymer which can have an aromatic ring, such as polystyrene, halogen-containing polystyrene, phenol resin, epoxy resin, halogen-containing epoxy resin, phenoxide resin, rosin, aromatic petroleum resin, polyvinyl naphthane, polyvinyl carbazole, etc., (B) is an aromatic organic solvent, such as xylene, naphthalene, quinoline, biphenyl, etc., and (C) is a compatible polymer, such as an alkyd resin, acrylic resin, etc.

(Effects of the Invention)

As described in detail hereinabove, considerable improvements can be achieved by the present invention. They are summarized as follows:

1. Improvement in workability

The filter sheet is simply inserted between the presser part and the parallel framing parts while the presser part is picked up. This process greatly contributes to easier filter making. The filter sheet is adhered only on the parallel framing parts, which results in high quality of preparation without deflection or distortion. Further, the filter frame is quite easily detachable because the filter sheet is conveniently sheared off between the presser part and the parallel framing parts.

2. Improvement in specimen stability

As the filter sheet is pressurized and fixed on the glass slide under the presser part when it is sheared off, its surface can be kept uniformly, so that no change in shape of the specimens results.

3. Improvement in preparation quality

The area of the filter sheet to be mounted is decreased remarkably and thus, the filter sheet never swells out of the glass slide when the sealing medium is added thereto. This safely prevents inclusion of unfavorable bubbles in the preparation

What is claimed is:

1. A method of making a filter for preparation which comprises forming a filter frame by cutting a flexible sheet of material to have an external size suitable to set on a glass slide, and slitting said filter frame to form two slits with a central hole therebetween; said two slits defining inner edges of parallel framing parts in said filter frame and outer edges of a presser part; pulling one end of said presser part upward; inserting a porous filter sheet between said presser part and the parallel framing parts; releasing said presser part downward and restoring said presser part to an original position, so that said filter sheet contacts an under surface of said presser part, is contained in said slits between said presser part and said parallel framing parts, adheres to an upper surface of said parallel framing parts, and a portion of said filter sheet is exposed through said central hole for receiving mounting specimens thereon.

* * * * *